United States Patent
McEwen

(10) Patent No.: US 8,840,579 B2
(45) Date of Patent: Sep. 23, 2014

(54) INTERNAL TOURNIQUET METHOD

(76) Inventor: James A. McEwen, Vancouver (CA)

( * ) Notice: Subject to any disclaimer, the term of this patent is extended or adjusted under 35 U.S.C. 154(b) by 731 days.

(21) Appl. No.: 13/166,675

(22) Filed: Jun. 22, 2011

(65) Prior Publication Data

US 2011/0251637 A1 Oct. 13, 2011

Related U.S. Application Data

(62) Division of application No. 11/381,627, filed on May 4, 2006, now Pat. No. 7,981,070.

(51) Int. Cl.
*A61N 1/30* (2006.01)
*A61M 1/00* (2006.01)
*A61M 31/00* (2006.01)
*A61M 29/00* (2006.01)

(52) U.S. Cl.
USPC ............ 604/19; 604/30; 604/31; 604/66; 606/191

(58) Field of Classification Search
USPC ........ 606/201–203, 191, 194; 604/65–67, 27, 604/30, 31, 32, 35, 29, 503–505, 19, 21, 604/22; 600/495, 500, 504, 505, 322, 600/325–327, 333, 371, 390; 356/425
See application file for complete search history.

*Primary Examiner* — Dianne Dornbusch
(74) *Attorney, Agent, or Firm* — Hancock Hughey LLP

(57) ABSTRACT

An internal tourniquet and method for establishing hemostasis within a portion of a limb to facilitate surgery controls flow of a fluid into a capsule surrounding substantially all of a human joint. Blood concentration in the capsule is sensed; and pressure in the capsule is controlled to maintain a fluid pressure in the capsule within a predetermined pressure tolerance window. The concentration of blood in the capsule is maintained below a predetermined maximum concentration while the fluid pressure is within the pressure tolerance window.

20 Claims, 1 Drawing Sheet

INTERNAL TOURNIQUET METHOD

FIELD OF THE INVENTION

This invention pertains to an internal tourniquet used for stopping blood flow within a joint capsule in a portion of a surgical patient's limb to facilitate the performance of a surgical procedure.

BACKGROUND OF THE INVENTION

External tourniquet systems have long been used to establish hemostasis in the upper and lower limb in order to facilitate orthopedic surgical procedures. External tourniquet systems of the prior art typically include a pneumatic tourniquet cuff applied around a patient's limb proximal to a desired surgical field, and an external tourniquet instrument for supplying the cuff with gas at a pressure above the minimum pressure needed to stop arterial bloodflow past the cuff and into the surgical field for the duration of a surgical procedure. In this way, an external tourniquet system establishes a bloodless and clear surgical field in the limb distal to the cuff, allowing complex orthopedic surgical procedures to be performed with improved accuracy, safety and speed. Many types of external tourniquet systems have been described in the prior art, such as those described by McEwen in U.S. Pat. Nos. 4,469,099, 4,479,494, 5,439,477 and McEwen and Jameson in U.S. Pat. Nos. 5,556,415 and 5,855,589. However, in addition to establishing a bloodless surgical field, external tourniquet systems of the prior art also stop bloodflow to non-surgical regions of the limb, resulting in ischemia and a risk of injury to these non-surgical regions that increases as the duration of ischemia increases. Further, external tourniquet systems of the prior art apply pressure to underlying muscle, blood vessels and nerves proximal to the surgical site, resulting in a risk of injury to these tissues that increases as the level of pressure and duration of pressure application increases. In addition, anatomical considerations in certain surgical procedures, such as in hip and shoulder surgeries, may limit or completely prevent the use of external tourniquet systems for establishing hemostasis.

If an external tourniquet system is not used, then other apparatus known in the prior art may be employed to improve visualization and reduce bleeding, especially for arthroscopic surgical procedures. Some prior-art apparatus manage the flow of sterile fluid into and out of a capsule that envelops a joint, thereby to help establish a pressure within the capsule that may reduce bleeding and improve visualization, and to help remove surgical debris and blood that may be present in the capsule. Prior-art fluid management systems for arthroscopic surgery are described, for example, by Chandler et al. in U.S. Pat. No. 5,800,383, by Beiser et al. in U.S. Pat. Nos. 5,840,060 and 5,662,611. Arthroscopic fluid management systems known in the prior art require significant manual intervention, knowledge, skill and attention by the surgeon throughout a surgical procedure in order to balance a number of competing requirements: the control of bleeding in the surgical field, the minimization of extravasation or swelling of tissues surrounding the surgical field and its associated risk of patient injury; the removal of blood and surgical debris from the surgical field; the maintenance of acceptable visualization; and the minimization of fluid loss and its related costs and hazards.

To facilitate new orthopedic surgical procedures that are becoming less invasive, as well as to facilitate arthroscopic surgical procedures that are becoming increasingly complex, there is a need for an internal tourniquet that can establish adequate hemostasis and provide a sufficiently bloodless surgical field over a time period suitably long for the performance of a surgical procedure without the limitations in performance and without the risks of patient injuries associated with prior-art external tourniquet systems and arthroscopic fluid management systems.

SUMMARY OF THE INVENTION

The present invention provides an internal tourniquet for safely controlling hemostasis within a joint capsule by maintaining a pressure within the joint capsule that is sufficient to compress blood vessels to stop blood flow, thus providing hemostasis around joints such as the hip or shoulder where conventional external tourniquets that require an external encircling cuff cannot be used.

DETAILED DESCRIPTION OF THE PREFERRED EMBODIMENT

Figure 1:
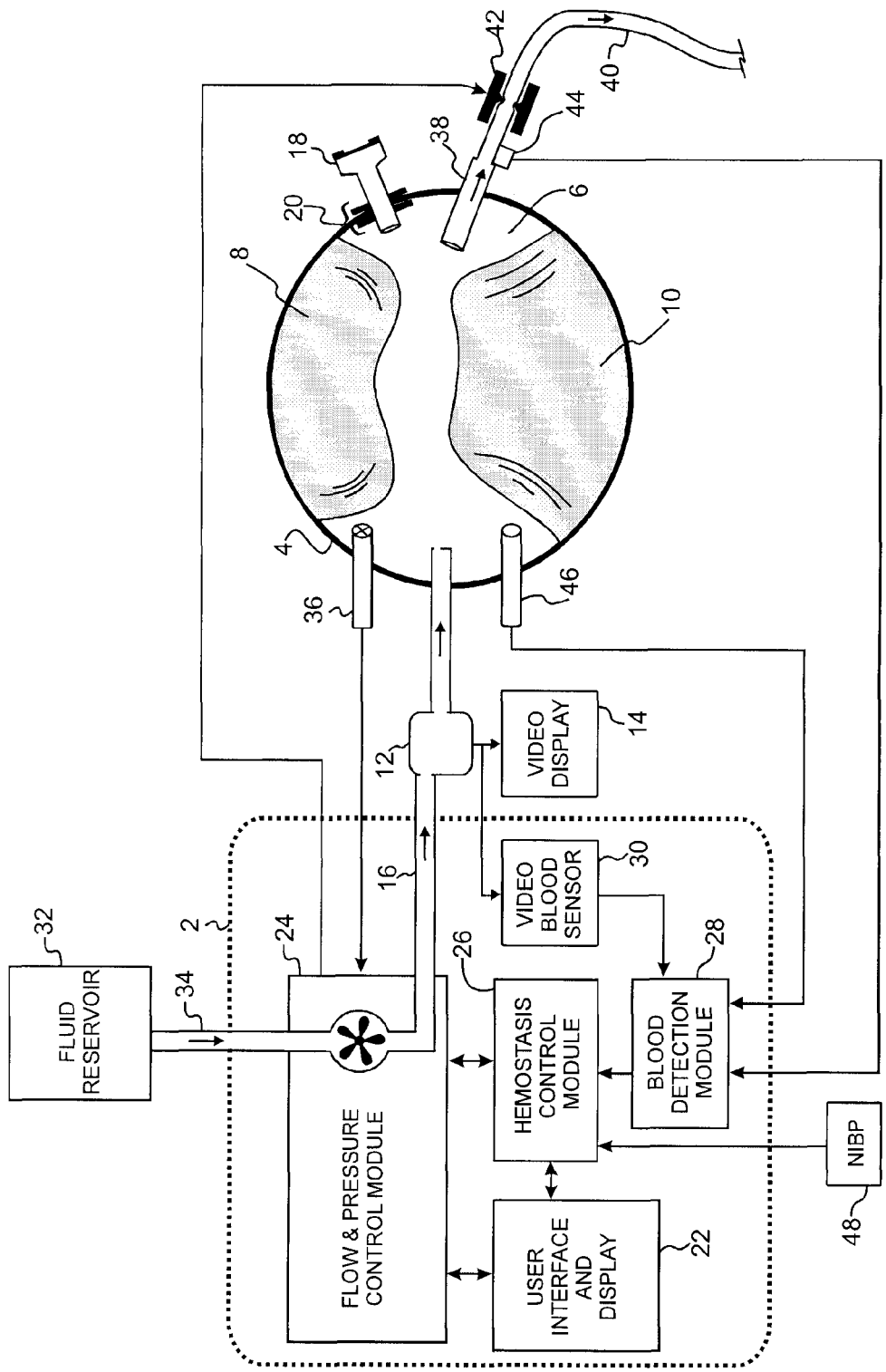
FIG. 1 is a block diagram of one preferred embodiment in an orthopedic surgical application.

A block diagram of a preferred embodiment of the invention in use during an orthopedic surgical procedure is depicted in FIG. 1. Internal tourniquet 2 supplies clear pressurized fluid to joint capsule 4 to permit a surgical procedure to be performed within the region 6 enclosed by the joint capsule 4. Joint capsule 4 is a substantially fluid-tight sac-like envelope that encloses the cavity of a synovial joint by attaching to the circumference of the articular end of each involved bone 8 and 10.

To visualize the bones and tissues within the joint the operating surgeon inserts a scope 12 into the joint capsule 4. Scope 12 includes a cannulated sheath that provides a fluid passageway from internal tourniquet 2 to the interior region 6 of joint capsule 4, as shown in FIG. 1. Scope 12 is typical of commonly used scopes and contains fiber optic fibers coupled to a light source for transmitting light into joint capsule 4 and magnifying lenses coupled to a color video camera for visualizing the interior of region 6 of joint capsule 4. Video signals from the camera of scope 12 are transmitted to video display 14 for viewing by the operating surgeon and to internal tourniquet 2 for analysis as described below. Pressurized fluid from internal tourniquet 2 is supplied to scope 12 via flexible plastic tubing 16.

Surgical instruments may be inserted into the joint capsule 4 via instrument portal 18. Instrument portal 18 forms a substantially fluid-tight seal around the body of a surgical instrument as it is inserted through the portal, the fluid-tight seal of instrument portal 18 may be adapted to accommodate surgical instruments of various diameters and shapes. Instrument portal 18 includes retaining elements 20 as shown in FIG. 1. Retaining elements 20 form a fluid-tight seal between the body of instrument portal 18 and joint capsule 4, thereby preventing fluid loss from the capsule and extravasation of fluid into surrounding tissues. Retaining elements 20 also provide robust fixation of the portal for the duration of the surgical procedure and improve retention of the portal while surgical staff insert, manipulate and remove surgical instruments.

During the time period of a surgical procedure bleeding may occur from tissues and bones within region 6 of joint capsule 4 and from the tissues surrounding joint capsule 4 where openings into the capsule have been made. The presence of blood within the region can impede the ability of the operating surgeon to clearly visualize both the interior of the joint and any surgical instruments that may be present within the region; this may result in unnecessary delays, an increase in the risk of patient injury and a decrease in the precision of the surgical procedure.

Internal tourniquet 2 acts to help improve visualization of the interior of joint capsule 4 by maintaining hemostasis within region 6 of joint capsule 4. Internal tourniquet 2 supplies pressurized fluid to the joint capsule via scope 12, and controls the pressure of the fluid within the joint capsule and rate of fluid flow through the joint capsule. As described further below, internal tourniquet 2 maintains hemostasis within joint capsule 4 by actively adjusting the fluid pressure and flow within the joint capsule in response to changes in the amount of blood detected within the fluid both within the joint capsule and exiting the joint capsule. To reduce extravasation, internal tourniquet 2 acts to maintain the fluid pressure near the lowest pressure necessary to maintain hemostasis over a time period suitably long for the performance of a surgical procedure.

As shown in FIG. 1, internal tourniquet 2 consists of the following functional modules: user interface and display 22, flow and pressure control module 24, hemostasis control module 26, blood detection module 28 and video blood sensor 30. Internal tourniquet 2 is supplied with fluid from fluid reservoir 32 via flexible plastic tubing 34. Fluid reservoir 32 contains sterile normal saline solution, lactated ringers solution or other clear and sterile fluid suitable for the pressurization of joint capsule 4.

User interface and display 22 includes a LCD panel for the display of: pressure values, flow rate values, sensed blood concentration values and alarm conditions. Hemostasis control parameters are also displayed; these include minimum and maximum pressure limits, minimum and maximum flow limits and the operating modes of hemostasis control module 26. A membrane key pad forms part of user interface and display 22 for the adjustment of hemostasis control parameters and operating modes. User interface and display 22 also includes an audio transducer for alerting the operator to alarm conditions.

Flow and pressure control module 24 within internal tourniquet 2 includes a pump that pressurizes fluid from fluid reservoir 32; the pressurized fluid is supplied to joint capsule 4 via tubing 16 and scope 12. Flow and pressure control module 24 responds to a fluid flow rate reference signal and a fluid pressure reference signal from hemostasis control module 26. Flow and pressure control module 24 acts to maintain the pressure within joint capsule 4 near the pressure level set by the fluid pressure reference signal and acts to maintain the fluid flow rate to joint capsule 4 near the rate set by the fluid flow rate reference signal.

Pressure transducer 36 generates a pressure signal. The level of the pressure signal is representative of the pressure of fluid sensed within region 6 of joint capsule 4. The pressure signal is communicated to flow and pressure control module 24. For clarity in FIG. 1, pressure transducer 36 is shown as a separate device extending into joint capsule 4; it will be apparent that pressure transducer 36 could be combined with scope 12, instrument portal 18 or other apparatus in direct communication with the fluid-filled region 6 of joint capsule 4.

The fluid supplied to joint capsule 4 by flow and pressure control module 24 is removed from joint capsule 4 through fluid outlet portal 38 and flexible plastic tubing 40. An outlet control valve 42 acts upon tubing 40 to control the rate at which fluid leaves joint capsule 4. In the preferred embodiment outlet control valve 42 is a servo controlled pinch valve which acts upon tubing 40 in response to an outlet control signal from flow and pressure control module 24. Fluid supplied to joint capsule 4 may also leave the joint capsule through extravasation, through instrument portal 18, and through surgical incisions extending into joint capsule 4.

By varying the degree of restriction in tubing 40 and the rate at which fluid is supplied to joint capsule 4, flow and pressure control module 24 acts to maintain the pressure level within joint capsule 4 and the fluid flow rate through joint capsule 4 near the levels set by hemostasis control module 26. In the preferred embodiment, fluid pressure and flow within joint capsule 4 are maintained near set levels with a controllable fluid pump and a variable outlet restriction, it will be apparent that other means may be used to maintain fluid flow through the capsule and pressure within the capsule near desired levels. For example, two pumps may be used, one supplying fluid to the capsule the other acting as a variable restriction or suction source to remove fluid from the capsule; as another example, fluid from a pressurized source could be supplied to the capsule through a controlled restricting valve and removed from the capsule via a controlled restricting valve or pump.

Flow and pressure control module 24 communicates the pressure signal and a flow rate signal representative of the rate of fluid flowing into the joint capsule 4 to hemostasis control module 26 and to user interface and display 22 for display to the user. The flow rate signal may be obtained by any suitable flow sensor or meter associated with the flow and pressure control module 24.

Blood detection module 28 receives and processes blood concentration signals from blood sensors 44 and 46 and video blood sensor 30. Blood sensors 44 and 46 are optical colorimetric sensors sensitive to the absorption spectra of hemoglobin, a hemoprotein composed of globin and heme that gives red blood cells their characteristic red color. Blood sensors 44 and 46 transmit light with predetermined wavelengths through a volume of fluid to a photodetector to produce signals indicative of the light absorption, hence the amount of hemoglobin detected within the fluid, which is representative of the concentration of blood present within the fluid. Blood sensor 44 (BLD-6.0, Edgewood, N.Y.) is shown in FIG. 1 applied to tubing 40 that is external to the joint capsule 4. This sensor detects the amount of hemoglobin present in a predetermined sample volume of fluid exiting the joint capsule through outlet portal 38 and tubing 40. Blood sensor 46 operates on similar principles to sensor 44 and is inserted directly into the joint capsule. It also produces a signal indicative of the amount of hemoglobin present within a predetermined sample volume of fluid within joint capsule 4. For clarity in FIG. 1, blood sensor 46 is shown as a separate device extending into joint capsule 4; it will be apparent that blood sensor 46 could form part of scope 12, instrument portal 18 or other apparatus in direct communication with the fluid-filled region 6 of joint capsule 4.

Video blood sensor 30 receives video signals from the color video camera that forms part of scope 12 and analyses these video signals to determine the concentration of blood present in the fluid within the visual field of the scope. Video blood sensor 30 produces a video blood concentration signal indicative of the amount of blood sensed within the visual field of the scope that is communicated to blood detection module 28. Video blood detector contains a computer processor with software algorithms that digitize and analyze in real time the video signals from the video camera of scope 12. The video analysis algorithms identify red colored regions of the visual field. The probability that a region contains a concentration of blood is computed based on: the detected features present within the region, a comparison with surrounding regions; and a comparison with regions in previous video frames. Identified regions with a computed probability that exceed a predetermined minimum probability threshold are then quantified to determine the level of the video blood concentration signal communicated to blood detection module 28.

Blood detection module 28 receives inputs from blood sensors 44, 46 and video blood sensor 20. Blood detection module contains algorithms to prioritize, compare and assign weighting values to the blood concentration signals from the sensors and produces a detected blood concentration signal; the level of this signal is indicative of the amount of blood present within joint capsule 4. This detected blood concentration signal is communicated to hemostasis control module 26 and user interface and display 22. Although three different blood sensors are shown and described in the preferred embodiment it will be apparent that blood detection module 28 may be adapted to produce a detected blood concentration signal from a lesser or greater number of blood sensors and may be adapted to accept signals from blood sensors based on other measurement principles.

The hemostasis control module 26 of internal tourniquet 2 receives the detected blood concentration signal from blood detection module 28 and receives hemostasis control parameters from user interface and display 22. Hemostasis control module 26 also receives the pressure and flow rate signals from flow and pressure control module 24. Hemostasis control module 26 produces the fluid pressure reference signal and the fluid flow rate reference signal which are communicated to flow and pressure control module 24. As described above, the levels of these signals control the fluid pressure and the flow rate that fluid control module 24 will maintain in region 6 of joint capsule 4.

Hemostasis control module 26 acts to maintain a bloodless surgical field by automatically adjusting the levels of the fluid pressure and fluid flow rate reference signals in response to changes in the level of the detected blood concentration signal.

Hemostasis control module 26 adjusts the level of the fluid pressure reference signal so that the pressure signal is maintained at a level between the minimum pressure limit and the maximum pressure limit. Hemostasis control module 26 also adjusts the level of the fluid flow rate reference signal so that the flow rate signal is maintained at a level between the minimum flow rate limit and the maximum flow rate limit. The values of the minimum and maximum pressure and flow limits may be set individually by an operator of internal tourniquet 2 via user interface and display 22 or be set automatically to predetermined values by hemostasis control module 26.

If for any reason, hemostasis control module 26 and fluid and pressure control module 24 cannot maintain the pressure signal at a level that is within the pressure tolerance window formed by the minimum and maximum pressure limits an alarm signal is generated when the pressure signal is outside the tolerance window. For example if the minimum pressure limit is set at 10 mmHg and the maximum pressure limit is set at 50 mmHg, the alarm signal will be generated if the fluid pressure is less that 10 mmHg or greater than 50 mmHg. The alarm condition is indicated to the operator by user interface and display 22. Similarly, if the level of the flow rate signal cannot be maintained within the flow tolerance window formed by the minimum and maximum flow rate limits an alarm signal is also generated to alert the user that that internal tourniquet 2 cannot maintain the desired pressures or flows.

Examples of some conditions that may cause alarms are: the occlusion of outlet portal 38 or tubing 40 by surgical debris; substantial fluid leaks from joint capsule 4; occlusion of tubing 16 or the fluid pathway within scope 12, and failure of capsule pressure sensor 36.

Hemostasis control module 26 has two operating modes: pressure-preferred mode and flow-preferred mode. The operating mode of hemostasis control module 26 may be set by the operator via user interface and display 22 or may be set automatically by hemostasis control module 26 in response to predetermined fluid pressure levels, fluid flow rates and region blood concentrations.

When operating in pressure-preferred mode, hemostasis control module 26 maintains the fluid pressure reference signal at a constant level and responds to an increase in the amount of blood present within region 6, as indicated by the level of the detected blood concentration signal, by proportionally increasing the level of the fluid flow rate reference signal. This causes an increase in fluid flow through joint capsule 4 which acts to clear blood from the capsule and restore a clear operating field. When the concentration of blood detected in the capsule decreases, the fluid flow rate reference signal is also decreased by hemostasis control module 26 until the level of the flow rate signal is near the minimum flow rate limit, this acts to conserve the fluid in fluid reservoir 32. When adjusting the fluid flow rate reference signal, hemostasis control module 26 maintains the level of the flow rate signal within the minimum and maximum fluid flow rate limits. If, while adjusting the fluid flow rate reference signal to control bleeding within the region 6, hemostasis control module 26 increases the fluid flow rate reference level to the maximum flow rate limit and the level of the detected blood concentration signal exceeds a predetermined maximum level, an alarm signal is generated to indicate to surgical staff that internal tourniquet 2 cannot adequately control the bleeding within the region 6.

When operating in flow-preferred mode, hemostasis control module 26 maintains the fluid flow rate reference signal at a constant level and responds to an increase in the amount of blood present within region 6, as indicated by the level of the detected blood concentration signal, by increasing the level of the fluid pressure reference signal. This causes an increase in fluid pressure within joint capsule 4 which acts to prevent blood from entering the capsule and obscuring the operating field. When adjusting the fluid pressure reference signal hemostasis control module 26 maintains the level of the fluid pressure signal within the minimum and maximum fluid pressure limits. If while adjusting the fluid pressure reference signal to control bleeding within the region 6, hemostasis control module 26 increases the fluid pressure reference level to the maximum pressure limit and the level of the detected blood concentration signal exceeds a predetermined minimum level an alarm signal is generated to indicate to a user that internal tourniquet 2 cannot control the bleeding within the region 6.

To continuously maintain a bloodless surgical field for the duration of a surgical procedure, hemostasis control module 26 may be adapted to automatically change operating modes and vary the minimum pressure and flow limits, in response to changes in the level of the detected blood concentration signal and pressure and flow rate signals.

In FIG. 1 an external non-invasive blood pressure (NIBP) monitor 48 is shown in communication with hemostasis control module 26. NIBP monitor 48 is an external device that non-invasively measures the blood pressure (BP) of the surgical patient. For example, the NIBP monitor may measure BP intermittently using an oscillometric technique, or may measure BP continuously using pulse wave transit time. NIBP monitor 48 produces a BP signal indicative of the value of the patient's systolic blood pressure which is communicated to hemostasis control module 26. In response to hemostasis control parameters set by an operator via user interface and display 22, hemostasis control module 26 may operate to make adjustments in the level of the fluid pressure reference signal in response to changes in the patient's blood pressure. For example, if the patient's blood pressure rises hemostasis control module 26 can increase the fluid pressure within the window formed by the minimum and maximum fluid pressure limits. Similarly, if the patient's blood pressure decreases hemostasis control module 26 can decrease the fluid pressure. By acting in response to changes in the BP signal to adjust the fluid pressure within region 6, hemostasis control module 26 can better maintain a bloodless surgical field. It will be apparent that other devices and methods could be used to determine the systolic blood pressure and that hemostasis control module 26 could similarly respond to systolic blood pressure signals produced by other external devices. It will also be apparent that an NIBP monitor could be incorporated within internal tourniquet 2 to eliminate the need for a separate device.

For clarity the preferred embodiment described above has been shown controlling hemostasis within the region enclosed by the substantially fluid-tight capsule of an articulating joint. The embodiment described may be adapted to help control hemostasis during other minimally invasive surgical procedures within a partially open or open region near a joint or bone where a bloodless surgical field must be maintained.

The embodiment illustrated is not intended to be exhaustive or limit the invention to the precise form disclosed. It is chosen and described in order to explain the principles of the invention and its application and practical use, and thereby enable others skilled in the art to utilize the invention.

The invention claimed is:

1. A method of operating an internal tourniquet for controlling hemostasis near a human joint that includes a region through which fluid may be directed to flow, comprising the steps of:
    sensing the amount of blood in the region;
    adjusting the fluid flow rate through the region in response to changes in the amount of blood sensed in the region.

2. The method of claim 1 wherein the adjusting step includes maintaining the concentration of sensed blood below a maximum concentration level over a time period suitably long for the performance of a surgical procedure.

3. The method of claim 2 wherein the adjusting step includes controlling the rate of fluid flow into the region.

4. The method of claim 3 wherein the adjusting step includes controlling the rate of fluid flow out of the region.

5. The method of claim 1 wherein the sensing step includes indicating the amount of hemoglobin present in the fluid in the region.

6. The method of claim 5 including the step of producing an indication of the amount of hemoglobin present in the fluid by measuring the absorption of light directed through the fluid.

7. The method of claim 5 including the step of producing an indication of the amount of hemoglobin present in the fluid by measuring the absorption of light of various wavelengths directed through the fluid.

8. The method of claim 1 wherein the sensing step includes measuring the amount of hemoglobin present in the fluid flowing out of the region though the substantially fluid-tight conduit.

9. The method of claim 1 including the step of adjusting the level of fluid pressure in the capsule in response to changes in the amount of blood sensed in the capsule.

10. The method of claim 1 including the step of monitoring the pressure in the capsule and maintaining the fluid pressure therein within a pressure tolerance window.

11. An internal tourniquet method for establishing hemostasis within a portion of a limb to facilitate surgery, comprising the steps of:
    facilitating flow of a fluid into a capsule surrounding the limb portion;
    sensing a concentration of blood in the fluid within the capsule;
    regulating in response to the sensed blood concentration the fluid flow the concentration of blood in the fluid in the capsule, and
    maintaining fluid pressure in the capsule within a pressure tolerance window.

12. The method of claim 11 wherein the sensing step includes controlling fluid outflow from the capsule to maintain the concentration of blood in the capsule below a maximum level.

13. The method of claim 11 including the step of sensing a level of fluid pressure in the capsule and controlling the fluid delivery means to maintain the fluid pressure in the capsule within the pressure tolerance window.

14. The method of claim 11 including the step of indicating the amount of hemoglobin present in the fluid in the capsule.

15. The method of claim 11 wherein the sensing step includes indicating the amount of hemoglobin present in the fluid in the capsule by measuring absorption of light that is directed through the fluid in the capsule.

16. The method of claim 11 including the step of producing an alarm signal if the sensed concentration of blood is greater than a maximum concentration level.

17. An internal tourniquet method comprising the steps of:
    directing flow of a fluid through a region near a human joint;
    sensing a concentration of blood in the fluid in the region;
    producing a blood signal indicative of the concentration of blood in the fluid;
    controlling the fluid flow to maintain a fluid pressure in the region within a pressure tolerance window; and
    controlling the fluid flow to maintain the concentration of blood below a maximum concentration level when the fluid pressure is within the pressure tolerance window.

18. The method of claim 17 including the steps of:
    sensing a level of fluid pressure in the region; and
    maintaining the fluid pressure in the region within the pressure tolerance window.

19. The method of claim 18 including the step of producing a pressure alarm signal if the level of the sensed fluid pressure is outside the pressure tolerance window.

20. The method of claim 17 including the step of producing a blood alarm signal if the sensed concentration of blood is greater than the maximum concentration level.

* * * * *

UNITED STATES PATENT AND TRADEMARK OFFICE
CERTIFICATE OF CORRECTION

PATENT NO. : 8,840,579 B2  
APPLICATION NO. : 13/166675  
DATED : September 23, 2014  
INVENTOR(S) : J. McEwen Page 1 of 1

It is certified that error appears in the above-identified patent and that said Letters Patent is hereby corrected as shown below:

In the Claims

Col. 8, line 19, in Claim 11, line 9: "the fluid flow" should be deleted.

Signed and Sealed this
Second Day of December, 2014

Michelle K. Lee
*Deputy Director of the United States Patent and Trademark Office*